(12) United States Patent
Fogwill et al.

(10) Patent No.: US 10,151,733 B2
(45) Date of Patent: Dec. 11, 2018

(54) CATALYTIC OXIDATION OF POLAR MODIFIERS IN CHROMATOGRAPHIC MOBILE PHASES

(71) Applicant: Waters Technologies Corporation, Milford, MA (US)

(72) Inventors: Michael O. Fogwill, South Grafton, MA (US); Joseph D. Michienzi, Plainville, MA (US); James P. Murphy, Franklin, MA (US)

(73) Assignee: Waters Technologies Corporation, Milford, MA (US)

( * ) Notice: Subject to any disclaimer, the term of this patent is extended or adjusted under 35 U.S.C. 154(b) by 62 days.

(21) Appl. No.: 14/484,350

(22) Filed: Sep. 12, 2014

(65) Prior Publication Data

US 2015/0079691 A1    Mar. 19, 2015

Related U.S. Application Data

(60) Provisional application No. 61/877,607, filed on Sep. 13, 2013.

(51) Int. Cl.
 *G01N 30/84*   (2006.01)
 *G01N 30/68*   (2006.01)
 *G01N 27/62*   (2006.01)

(52) U.S. Cl.
 CPC .............. *G01N 30/84* (2013.01); *G01N 30/68* (2013.01); *G01N 27/626* (2013.01); *G01N 2030/8435* (2013.01)

(58) Field of Classification Search
 CPC ...... G01N 30/84; G01N 27/626; G01N 30/68; G01N 2030/8435
 See application file for complete search history.

(56) References Cited

U.S. PATENT DOCUMENTS 3,762,878 A * 10/1973 Villalobos .............. G01N 1/405
 422/54
5,777,141 A * 7/1998 Brunner ................. B01D 15/40
 554/175

(Continued)

OTHER PUBLICATIONS

Agrell, J. et al., "Production of hydrogen from methanol over Cu/ZnO catalysts promoted by ZrO2 and Al2O3," Journal of Catalysis, 2003, vol. 219, 389-403.

(Continued)

*Primary Examiner* — Lyle Alexander
*Assistant Examiner* — Dwan A Gerido
(74) *Attorney, Agent, or Firm* — Womble Bond Dickinson (US) LLP; Deborah M. Vernon; Rebecca N. Barnes (57) ABSTRACT

The present disclosure relates to an oxidizer, and related methods, for oxidizing polar modifiers in chromatographic mobile phases. The oxidizer enables the use of flame-based detection in chromatographic separations, such as carbon dioxide based chromatography, which employ polar modifiers, such as methanol. Upon exiting a chromatographic column, the mobile phase containing the polar modifier is flowed through an oxidizer that contains a catalyst to oxidize at least a portion of the polar modifier to a species that does not interfere with the function of the flame-based detector. The oxidizer allows for flame-based detection, such as flame ionization detection, in applications in which a polar modifier with a reduced form of carbon is used.

18 Claims, 3 Drawing Sheets

(56) References Cited

U.S. PATENT DOCUMENTS

| | | | |
|---|---|---|---|
| 5,866,004 A * | 2/1999 | Houck | B01D 11/0203 |
| | | | 210/136 |
| 2005/0178747 A1 | 8/2005 | Shibamoto | |
| 2006/0213875 A1 | 9/2006 | Shibamoto | |
| 2011/0113866 A1 * | 5/2011 | Finlay | G01N 30/6095 |
| | | | 73/61.52 |
| 2012/0077664 A1 * | 3/2012 | Jangbarwala | B01J 21/18 |
| | | | 502/1 |

OTHER PUBLICATIONS

Mah, C. et al., "An improved interface for universal acoustic flame detection in modified supercritical fluid chromatography," Journal of Separation Science, 2008, vol. 31, 1314-1321.

McCabe, R. W. et al., "Kinetics and reaction pathways of methanol oxidation on platinum", Journal of Physical Chemistry, 1986, vol. 90, 1428-1435.

Thurbide, K. B. et al., "Packed-column supercritical fluid chromatography with splitless flame ionization detection," Canadian Journal of Chemistry, 2004, vol. 82, 479-482.

* cited by examiner

Figure 3

CATALYTIC OXIDATION OF POLAR MODIFIERS IN CHROMATOGRAPHIC MOBILE PHASES

CROSS-REFERENCE TO RELATED APPLICATIONS

This application claims priority to U.S. Provisional Application No. 61/877,607 filed Sep. 13, 2013, which is incorporated herein by reference in its entirety.

TECHNICAL FIELD

The present disclosure relates to an oxidizer, and related methods, for use with flame-based detection in chromatographic separations that employ polar modifiers, such as methanol, as part of the mobile phase. The oxidizer functions by facilitating the oxidization of the polar modifiers in the mobile phase, such as a carbon dioxide based mobile phase, wherein the oxidizer and oxidization do not substantially disrupt the performance of the separation or the operation of the flame-based detector.

BACKGROUND

Flame-based detection is a common technique used in chromatography (e.g. gas chromatography) to detect analytes of interest (e.g. organic compounds) in an analyte stream. For instance, flame ionization detection (FID) functions by maintaining a flame via the addition of a combustible fuel (e.g. hydrogen) and an oxidant (e.g. air or oxygen) to the detector. An analyte stream (e.g. the eluent from a gas chromatography column) passes through the flame in the flame ionization detector. Compounds that contain a reduced form of carbon (e.g. organic compounds from the analyte stream that contain C—H bonds) are ionized in the flame to produce carbon-based ions and free electrons, while compounds without reduced carbon such as carbon dioxide, nitrogen and noble gases (e.g. helium) do not form free electrons. The newly-generated free electrons are attracted to a positive electrode (e.g. anode) while the carbon-based ions are attracted to a negative electrode (e.g. cathode) above the flame. As the ions and electrons reach their respective electrodes, an electric current is established. The amount of current flow is thus proportional to the number of carbon atoms entering the flame ionization detector. Accordingly, flame ionization detectors are very selective for, and can accurately measure the presence of, analytes that contain a reduced form of carbon (e.g. organic compounds).

In general, there are a number of different mobile phase fluids used in chromatography. Various chromatographic systems can use different mobile phase fluids depending on the nature of the separation to be carried out. For instance, any one of liquid acetonitrile, helium gas, or carbon dioxide can serve as a mobile phase in a chromatographic context. In addition, while operating with, for instance, a carbon dioxide mobile phase, modifiers can be added to the mobile phase to change the mobile phase net polarity and separation characteristics.

Although mobile phase polar modifiers such as methanol can serve to enhance the separation of analytes in a given sample of interest, many modifiers (e.g. methanol) contain a reduced form of carbon and therefore respond in a flame-based detector (e.g. a flame ionization detector). Because a polar modifier can be present in an amount much greater than the analyte of interest, the response from the flame-based detector to the polar modifier can overwhelm the response from the flame-based detector to the analyte of interest.

SUMMARY OF THE TECHNOLOGY

The present technology is directed to apparatus, and related methods, for the oxidation of polar modifiers (e.g. methanol) to compounds with a negligible response in a flame-based detector (e.g. carbon dioxide) or compounds that do not substantially produce a signal within a flame-based detector (e.g. hydrogen gas). Oxidation of the polar modifier or polar modifiers occurs downstream of the chromatography column in order to preserve the separation benefits of a modified mobile phase in the chromatography column. Oxidation of the polar modifiers before they reach a flame-based detector (e.g. a flame ionization detector) prevents them from interfering with the operation of the detector, and enables the use of flame based detection in chromatographic separations that employ polar modifiers (e.g. methanol) within the mobile phase.

One or more embodiments of the present technology feature a catalytic substrate in fluid communication with a mobile phase used in a chromatographic separation. For example, when a mobile phase containing a polar modifier (e.g. carbon dioxide containing methanol) and an analyte of interest exits a chromatography column, the analyte stream (i.e. the mobile phase and analyte of interest) is directed to contact a catalytic substrate located within an oxidizer downstream of the column outlet. The catalytic substrate within the oxidizer facilitates the oxidization of the polar modifier (e.g. methanol) to a compound that either does not respond in a flame-based detector, such as carbon dioxide, or to a compound that does not substantially produce a signal within the flame-based detector, such as hydrogen gas. In preferred embodiments, the oxidation of the polar modifier (e.g. methanol) is complete or substantially complete (e.g. from methanol to carbon dioxide). In some embodiments, incomplete or substantially incomplete oxidation (e.g. partial oxidation from methanol to formaldehyde or formic acid) can still give rise to species that produce a signal in the flame-based detector, thereby interfering with the operation of the detector. Also in some embodiments, the catalyst is selective or substantially selective for the modifier (e.g. methanol) and does not oxidize, partially or completely, the analyte of interest.

In one aspect, the present disclosure relates to an oxidizer for use in a chromatographic system, comprising an inlet capable of receiving a mobile phase containing a polar modifier, a chamber in fluid communication with the inlet port, wherein the chamber has a catalyst capable of oxidizing at least a portion of the polar modifier, and an outlet in fluid communication with the chamber capable of exiting the mobile phase and oxidized polar modifier from the chamber.

In another aspect, the present disclosure relates to a method of oxidizing a polar modifier in a chromatographic mobile phase, comprising providing a chromatographic system having a separation column, an oxidizer in fluid communication with and downstream of the column, and a flame-based detector in fluid communication with and downstream of the oxidizer, and oxidizing at least a portion of the polar modifier in the oxidizer, wherein the oxidizer has a catalyst capable of oxidizing at least a portion of the polar modifier.

In another aspect, the technology is directed to a method for oxidizing one or more polar modifiers within a chromatographic mobile phase containing an analyte(s) of interest. The method includes providing a chromatographic system defining a flow path and flowing the mobile phase and modifier or modifiers through a separation column along the flow path to separate analytes based on a defined physical property, and oxidizing at least a portion of the polar modifier with a flow-through oxidizer located along the flow path downstream of the separation column, wherein the oxidizer contains a catalyst to facilitate oxidation of the polar modifier.

The above aspects can include one or more of the following features. In one embodiment, the mobile phase of the chromatographic system includes carbon dioxide. For instance, carbon dioxide is a component of the mobile phase (e.g. the mobile phase is majority carbon dioxide, a mixture of carbon dioxide and methanol, or a gradient elution of carbon dioxide and methanol). In some embodiments, the mobile phase comprises a fluid and a polar modifier (e.g. methanol). In some embodiments, the chromatographic system is a supercritical fluid chromatographic system. The technology can further include detecting at least a portion of the analyte using a detector located along the flow path downstream of the oxidizer. The catalyst can include Ag, Au, Rh, Ni, Cd, Pt, Pd, Cu, $TiO_2$, ZnO, $ZrO_2$, $Al_2O_3$, or combinations, alloys, or other mixtures thereof. It can also be deposited on the surface of a ceramic support, such as, but not limited to, zirconia, titania, silica, alumina or any combination thereof. The support can be formed from a porous monolithic structure, a partially monolithic structure (e.g. partially sintered particles or a porous preform) or a bed of particles. In certain embodiments, the technology further includes the use of a temperature controller (e.g. heater) in thermal communication with the oxidizer to maintain the catalyst at a desired temperature range. In one or more embodiments of the above aspect, oxidation of a least a portion of the one or more mobile phase polar modifiers can include substantially complete oxidation of the modifier. In one or more embodiments, an oxygen source or oxygen gas may be supplied to the oxidizer or catalyst bed to effect, increase or improve oxidation.

In another aspect, the technology features a chromatographic system defining a flow path. The chromatography system includes a mobile phase for use in the flow path and containing an analyte(s) of interest and one or more polar modifiers, a separation column disposed along the flow path of the mobile phase capable of separating the analyte based on a defined physical property, and an oxidizer located along the flow path of the mobile phase downstream of the separation column, the oxidizer containing a catalyst capable of facilitating oxidation of the one or more polar modifiers within the mobile phase.

The above aspects can include one or more of the following features. For instance, the system can include a detector located along the flow path downstream of the oxidizer. The detector can be a flame ionization (FID) detector. The system can further include a temperature controller in thermal communication with the oxidizer capable of maintaining the catalyst at a desired temperature range. In one or more embodiments of the above aspect, oxidation of a least a portion of the one or more mobile phase polar modifiers can include substantially complete oxidation of the modifier.

The present technology provides a number of advantages over current apparatus and methods. For instance, the technology allows a user to operate a chromatographic system with a polar modifier (e.g. methanol) as a component of the mobile phase (e.g. carbon dioxide) in combination with a flame-based detector without substantially masking or compromising the detector response to the analyte(s) of interest. The present technology also enables a user to expand the applicable analyte range for a chromatographic separation via the use of a polar modifying agent while still maintaining the convenience, reliability and universal response of a conventional flame-based detector. A user can also employ a conventional flame-based detector for a wider range of chromatographic separations, and thus save on the costs of specialized equipment for detection of analytes in a mobile phase flow stream that contains a polar modifier. The present technology can make chromatographic separations employing polar modifiers more convenient to perform, because flame-based detectors (e.g. flame ionization detectors) are easy to use and are much simpler than for instance a mass spectrometer, evaporative light scattering detector, or other types of detectors. For example, flame-based detectors have a wider dynamic range than mass spectrometry or evaporative light scattering detectors. These detectors are also more sensitive evaporative light scattering detectors. Moreover, the technology allows a user to save time by obviating the need to otherwise account for the presence of combustible polar modifiers in a mobile phase flow stream when using a flame-based detector.

BRIEF DESCRIPTION OF THE DRAWINGS

The features and advantages of the technology described above, taken together with further advantages, can be better understood by referring to the following description taken in conjunction with the accompanying drawings. The drawings are not necessarily to scale, emphasis instead generally being placed upon illustrating the principles of the technology.

DETAILED DESCRIPTION

The present technology is directed to an oxidizer, and related methods, for oxidizing a polar modifier (e.g. methanol) to a species that does not substantially produce a signal (e.g. carbon dioxide) in a flame-based detector (e.g. a flame ionization detector). The polar modifier (e.g. methanol) can be added to a chromatographic mobile phase. The mobile phase can be heated or pressurized and can exist in a number of physical states (e.g. gas, liquid, or supercritical fluid). In some preferred embodiments, the mobile phase includes carbon dioxide.

The present technology is applicable to chromatographic systems having a wide range of mobile phase flow rates. The flow rate can vary depending on the system, the mobile phase, the sample, the conditions, the gradient etc. The mobile phase mass flow rate can vary between about 0.005 and 10 g/min. In some embodiments, the amount mass flow rate is at least 0.005, 0.01, 0.05, 0.1, 0.5, 1, 2, 5 or 10 g/min. These values can also define a range of mass flow rates, e.g., 0.01 to 0.5 g/min. In particular, the mass flow rate can vary between about 0.005 and 0.1 g/min for microfluidic applications, and between about 0.5 and 10 g/min for analytical-scale applications. The flow can also be split prior to the FID. The mass flow rate at the detector can vary between about 0.005 and 0.1 g/min for microfluidic applications (i.e., full flow introduced to detection), and about 0.020 and 0.5 g/min for a split-flow analytical-scale applications.

Polar modifiers are added to chromatographic systems that use fluids such as carbon dioxide as a mobile phase to enhance the separation. Carbon dioxide is a substantially nonpolar mobile phase and is not polar enough to substantially elute some polar analytes from a chromatographic column. Addition of a polar modifier (e.g. methanol) to a mobile phase (e.g. carbon dioxide) increases the polarity of the mobile phase and allows the mobile phase to dissolve more polar analytes and thereby carry them through a chromatographic column. This, in turn, expands the applicable range of analytes for a chromatographic separation.

The amount of polar modifier in the mobile phase can vary depending on the system, the mobile phase, the sample, the conditions, the gradient, etc. The amount of polar modifier present in the mobile phase can vary between about 1 and 50%. In particular, the amount of polar modifier present in the mobile phase can vary between about 2 and 20%. In some embodiments, the amount of polar modifier present in the mobile phase is at least 1, 2, 3, 4, 5, 6, 7, 8, 9, 10, 12, 14, 16, 18, 20, 22, 24, 26, 28, 30, 35, 40, 45 or 50%. These values can also define a range of polar modifier present in the mobile phase, e.g., 2% to 5%, or 9% to 16%.

The present technology makes use of catalytic substrates to oxidize polar additives, such as methanol or other polar modifiers, to carbon dioxide or other more oxidized forms in the context of chromatography. For instance, in some embodiments the technology provides catalytic substrates that are specially adapted to oxidize or modify substrates that are commonly used in the context of chromatography. Moreover, in some embodiments, the technology is specially adapted to minimize dead volume within a chromatographic system, thereby minimizing band broadening of peaks. For instance, the technology can be geometrically and fluidically optimized so as to minimize concerns relating to dead volume and multiple pathways through the chromatographic system.

The amount of catalyst used to oxidize the polar additive in the mobile phase can vary depending on the type, purity, effectiveness, etc. of the catalyst and the flow rate of the mobile phase, polar modifier, or both, the type of mobile phase, polar modifier, or both, etc., the system, the conditions, etc. The amount of catalyst used to oxidize the polar additive (e.g., present in the oxidizer) relative to support can vary between about 0.01 and 100 wt % (e.g., filling the reactor vessel with pure silver). In particular, the amount of catalyst used to oxidize the polar additive (e.g., present in the oxidizer) relative to support can vary between about 0.2 and 100 wt %. For example, a chromatographic system can have a mobile phase flow rate starting at 1.5 g/min, use a 2-10% modifier gradient, and be split such that about 5% of the flow is directed toward a catalyst—detector system having 5.0 wt % catalyst to support.

The oxidization of polar modifiers in the mobile phase by the oxidizer can vary. In some embodiments, the oxidizer demonstrates substantially complete oxidation of the modifier. In other embodiments, the oxidizer demonstrates incomplete oxidation of the modifier. The oxidation of the modifier (e.g. methanol) can also result in the formation of an oxidized species that is capable of being further oxidized (e.g. formaldehyde, formic acid). Complete oxidation means that the carbon atom(s) of the polar modifier are oxidized to the highest oxidation state possible. For instance, the carbon atom within carbon dioxide has an oxidation number of +4, and the carbon atom cannot be further oxidized. Thus, oxidization of methanol to carbon dioxide represents complete oxidation of the carbon atom. Incomplete oxidization means that the carbon atom(s) of a polar modifier are oxidized to a compound(s) that is capable of undergoing further oxidation. For instance, the carbon atom within formaldehyde has an oxidation number of 0, and the carbon atom within formic acid has an oxidation number of +2. In both cases, the carbon atom can be further oxidized (e.g. to carbon dioxide), therefore oxidation of, for instance, methanol to formic acid represents incomplete oxidation.

Partially oxidized components such as formaldehyde and formic acid may respond in a flame-based detector, and may therefore disrupt the functioning the flame-based detector, such as an FID. Formic acid has a poor response in the FID; formaldehyde has a low of moderate response in the FID. It is not necessary, however, that fully 100% of the polar modifier is oxidized prior entering the flame-based detector. The present disclosure reduces or substantially eliminates polar modifiers from the mobile phase. The performance of a flame-based detector is improved by the mobile phase having reduced amounts of polar modifiers, and/or by minimizing the amount of incomplete oxidation products of polar modifiers (e.g. formic acid or formaldehyde). In one embodiment, the oxidizer oxidizes all, or substantially all, of the polar modifier (e.g. methanol) entering the oxidizer (e.g. to carbon dioxide). In another embodiment, greater than about 50% of the polar modifier (e.g. methanol) entering the oxidizer is completely oxidized to a species that is inert in the presence of a flame (e.g. carbon dioxide). Particularly, greater than about 60%, greater than about 70%, greater than about 80%, greater than about 90%, greater than about 95%, greater than about 99%, or greater than about 99.9% of the polar modifier entering the oxidizer is completely oxidized to a species that is inert in the presence of a flame (e.g. carbon dioxide).

The catalyst of the present disclosure is capable of oxidizing the polar modifiers present in a chromatographic mobile phase, as provided herein. In some embodiments, the catalyst is selected to ensure that it is capable of selectively oxidizing polar modifier solvents (e.g. methanol) within an analyte stream while not oxidizing analytes of interest (e.g. small molecules or peptides). If the catalyst preferably oxidizes, or substantially oxidizes, an analyte of interest, this can cause the analyte to behave differently in the presence of the flame and thus disrupt the operation of the flame-based detector. It is possible that partial oxidation of the analyte of interest (e.g. oxidation of a secondary alcohol to a ketone) may not have a substantially deleterious effect on the analyte's behavior in a flame-based detector. It is difficult to measure the effect that oxidation of the analyte has on the analyte's behavior in a flame-based detector. Therefore, oxidation of the analyte should be minimized. In one embodiment, less than about 50% of the analyte of interest is oxidized. Particularly, less than about 40%, less than about 30%, less than about 20%, less than about 10%, less than about 5%, less than about 1%, or less than about 0.1% of the analyte of interest is oxidized.

The present disclosure can also include converting at least a portion of the polar modifier (e.g. methanol) to hydrogen gas ($H_2$) or water via the addition of a reagent gas (e.g. oxygen, air, or another oxidant). The reagent gas can be introduced into the oxidizer or catalytic segment using the same inlet as the mobile phase or using a separate inlet. Such a conversion has the advantage of providing additional hydrogen fuel to the flame-based detector to help sustain the flame. A further advantage is that hydrogen gas and water does not contribute to the electric current in a flame ionization detector. For instance, the present technology can include any number of known catalysts, for instance the technology can include a catalyst such as $Cu/ZnO/ZrO_2/Al_2O_3$ that is capable of converting methanol to hydrogen gas (see e.g. Agrell et al. *J. Catalysis* (2003) 219 389-403, the contents of which are hereby incorporated by reference). Additionally, in some embodiments the present technology can include catalysts such as a nano-silver/zeolite film/copper grid (see e.g. Shen et al., *J. Catalysis*, 237 (2006) pp. 94-101 and references therein, the contents of which are hereby incorporated by reference).

The present technology does not require, or specify, a particular oxidative reaction through which polar modifiers (e.g. methanol) are converted to species that do not give a significant response in a flame-based detector (e.g. $H_2$ and/or $CO_2$). Without wishing to be bound by any particular theory, it is believed that one or more of the following reactions takes place on the surface of the catalyst within the oxidizer. Accordingly, Equations 1-3 are exemplary reactions to illustrate certain embodiments in which a polar modifier can be catalytically oxidized to a species such as carbon dioxide:

$$3O_2 + 2CH_3OH \rightarrow 2CO_2 + 4H_2O \qquad \text{Equation 1:}$$

$$O_2 + CH_3OH \rightarrow CO_2 + H_2 + H_2 \qquad \text{Equation 2:}$$

$$O_2 + RCH_2OH \rightarrow RH + CO_2 + H_2O \qquad \text{Equation 3:}$$

When converting the polar modifier to hydrogen gas, the oxidizer demonstrates substantially complete oxidation of the modifier. The formation of unwanted byproducts (e.g. formic acid) is minimized. In one embodiment, the oxidizer oxidizes all, or substantially all, of the polar modifier (e.g. methanol) entering the oxidizer to hydrogen gas. In another embodiment, greater than about 50% of the polar modifier (e.g. methanol) entering the oxidizer is converted to hydrogen gas. Particularly, greater than about 60%, greater than about 70%, greater than about 80%, greater than about 90%, greater than about 95%, greater than about 99%, or greater than about 99.9% of polar modifier entering the oxidizer is converted to hydrogen gas.

The catalyst of the present disclosure can include any number of catalysts known to catalyze the oxidation of polar compounds (e.g., alcohols) to oxidized species such as carbon dioxide. For instance, the catalyst can include Ag, Au, Rh, Ni, Cd, Pt, Pd, Cu, $TiO_2$, ZnO, $ZrO_2$, $Al_2O_3$, or combinations, alloys, or other compositions thereof (e.g., Pt/Pd, Cu/ZnO). In particular, the catalyst can be gold nanoparticles. The catalyst can also include a support and can be dispersed freely within an oxidizer. In some embodiments, the catalyst is deposited on the surface of a support, or contained on and/or in a semi-porous or fully porous support. For example, the catalyst can be deposited on the surface of a ceramic support, such as, but not limited to, zirconia, titania, silica, alumina or any combination thereof. In another example, the catalyst can be impregnated into a silica gel. The support can be formed from a porous monolithic structure, a partially monolithic structure (e.g., partially sintered particles or a porous preform), a honeycomb structure, a bed of particles, or a semi or fully porous sphere.

The catalyst can also include one or more promoters, such as metallic ions, $ZrO_2$, $Al_2O_3$, and combinations thereof. For example, both $ZrO_2$ and $Al_2O_3$ can be added as promoters to a catalyst formed of CU/ZnO. The amount of promoter used may be, for example, less than about 1 wt % of the catalyst. In one embodiment, the promoter comprises between about 0.001 and about 10 wt % of the total catalyst weight. The promoter may enhance one or more of the following characteristics including selectivity, reactant conversion, productivity, product yield, activity, stability, reducibility and regenerability. The promoter may be inactive as a catalyst when used alone or may have catalytic activity in absence of the catalyst.

Most catalysts are active and operate over a range of temperatures. Usually, this range is above about 25° C. (e.g. above room temperature). Certain catalysts are known to operate at a temperature well above 25° C. (e.g. 300° C. or higher). This can pose a difficulty in cases where heating of the catalyst is inconvenient. For instance, if the operating temperature range for a catalyst is above 400° C., the use of the catalyst between about 250-400° C. (e.g. typical FID temperatures) may result in less than optimal performance of the catalyst (e.g. substantially less than all methanol in contact with the catalyst is converted to carbon dioxide). In one embodiment, the catalyst operates between a temperature of about 100° C. and about 500° C. Particularly, the catalyst operates between a temperature of about 200° C. and about 500° C., about 300° C. and about 500° C. or about 400° C. and about 450° C.

Accordingly, the catalyst can also be contained within an oxidizer that is in thermal contact with a temperature controller (e.g. heater or an automatic heating element) that is capable of maintaining the catalyst at an optimal temperature. Additionally, in other embodiments, the heated portion of the flame-based detector can maintain the catalyst at an working temperature or temperature range. Other methods by which to maintain the catalyst at a working temperature or temperature range will be readily understood by one of skill in the art, for instance using ambient heat derived from a heated mobile phase.

The catalyst can be adapted to oxidize a polar modifier to carbon dioxide. In most cases, the polar modifier is methanol. The catalyst can be adapted to oxidize other polar modifiers, including but not limited to, trifluoroacetic acid, ammonium acetate, ammonium formate, phosphoric acid, formic acid, formamide, methylamine, dimethylamine, trimethylamine, chloroform, chloromethane, dichloromethane, chloroform, or combinations thereof. Particularly, the catalyst can be adapted to oxidize methanol, acetonitrile, methanolic ammonia, methanolic hydrochloric acid, trifluoroacetic acid, ammonium formate, formic acid, formamide, methylamine, dimethylamine, trimethylamine, oxalic acid, citric acid, chloromethane, dichloromethane, chloroform or combinations thereof.

Figure 1:
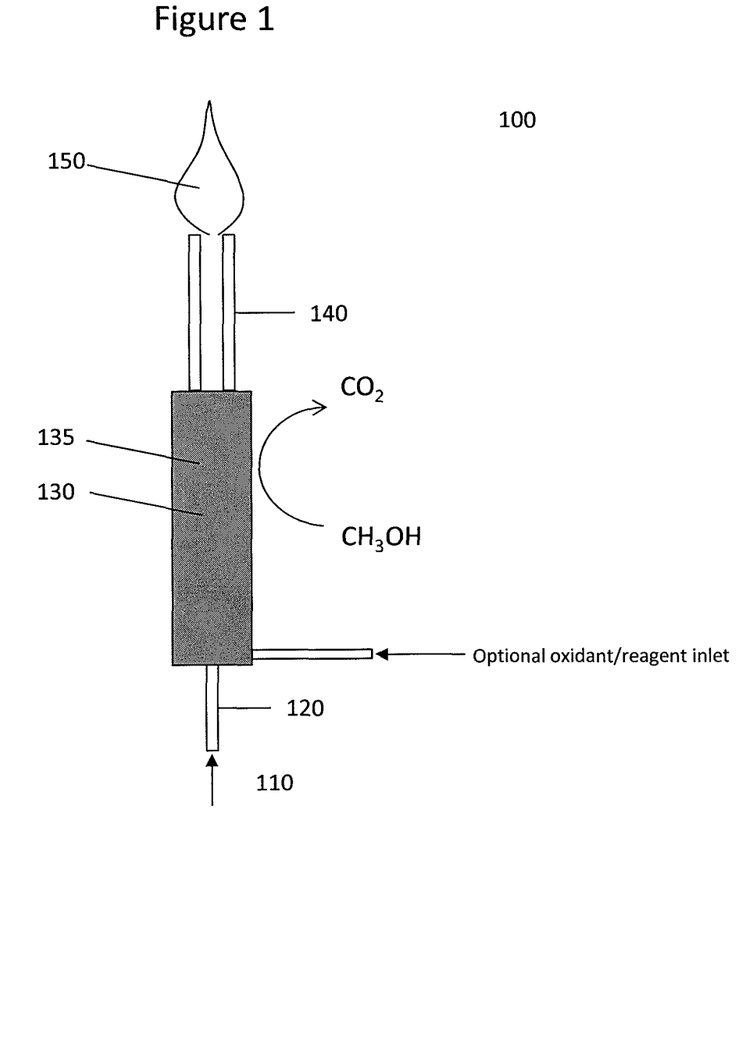
FIG. 1 is a schematic representation of the catalytic oxidation of methanol to carbon dioxide in the context of a chromatographic system with a flame-based detector.

FIG. 1 provides a schematic representation (100) of one embodiment of the present technology adapted for use with a flame ionization detector. It will be understood by one of skill in the art that FIG. 1 is an illustrative representation of the technology and should not be construed as limiting the scope of the invention. Column effluent (110) (e.g. an analyte(s) of interest, carbon dioxide and a polar modifier) enters the inlet (120) of the oxidizer (130). The oxidizer contains a catalyst (135) to facilitate oxidation of the polar modifier. Within the oxidizer, the polar modifier (e.g. methanol) is oxidized to carbon dioxide. The oxidizer is sized and oriented such that all or substantially all of the polar modifier is oxidized to carbon dioxide. The converted column effluent exits the oxidizer (130) and is immediately directed to a flame-based detector burner (140). The burner is adapted to burn hydrogen fuel and support a flame (150) which is capable of ionizing analytes which contain carbon for detection by the flame-based detector. The burner further contains an inlet for a combustible fuel (e.g. hydrogen) to support the flame. Some embodiments of the technology will not provide enough hydrogen gas from the oxidation of methanol to support the flame without a supplemental addition of combustible fuel.

The introduction of a component in a chromatographic system after the column, but before the detector can degrade the performance of the separation. Thus, the oxidizer is adapted to minimize the volume in which column effluent flows without being separated into constituent components, oxidized, detected, or otherwise acted upon. Such volume can be referred to in the art as 'dead volume' within a chromatographic system. Dead volume can have a deleterious effect on the efficiency of a chromatographic separation because such volume is known to contribute to reduced chromatographic performance (e.g. band broadening). Minimization of the dead volume is important for ensuring efficient chromatographic separation. The inlet (120) to the oxidizer can be adapted to match the size of the tubing or column carrying the column effluent, or other parameter, to reduce dead volume. The converted column effluent (130) can be directed immediately into a flame-based detector burner (140). The catalyst (135) can be dispersed within the oxidizer such that the catalyst displays a high surface area relative to its volume. A high ratio of surface area to volume is advantageous for a catalyst in which reactions occur on the surface of the catalyst. This ensures that the oxidizer containing the catalyst can be as small as possible while still enabling the catalyst to facilitate oxidation of all or substantially all of the polar modifier. All of these adaptations are advantageous for minimizing dead volume and thereby resulting in an efficient separation.

In most embodiments, the oxidizer is a flow-through apparatus which is integrated into a chromatographic system in fluid communication with a chromatographic column as well as a flame-based detector. The oxidizer is located downstream of the column and upstream of the detector. The polar modifier is oxidized within the detector as it flows from the column outlet to the detector. Such a flow-through oxidizer adds minimal dead volume, e.g. less than about 1%, less than about 0.1%, or less than about 0.01%, thereby minimizing the effects of band broadening within the chromatography apparatus.

The mobile phase (e.g. carbon dioxide) flow can be directed from the separation column to a splitter that separates a portion of the mobile phase for oxidation in the oxidizer and detection in a flame-based detector. Alternatively, all or substantially all of the mobile phase flow (e.g. column effluent) can be directed to the oxidizer and the flame-based detector. In some cases, a back pressure regulator, a fixed restrictor, or a thermally modulated variable restrictor can be used to maintain system pressure. Preferably, the oxidizer is placed in the mobile phase stream (e.g. column effluent) just upstream of the detector.

The present technology can be adapted for use in a number of different chromatographic systems. The technology can be used with preparative, semi-preparative, analytical, or capillary-scale packed-bed columns or open tubular columns. The columns can be prepared in conventional metallic, fused silica, or polymeric tubes or in metallic, ceramic, glass or polymeric microfluidic platforms of various internal diameter. The technology can be used with conventional gas chromatography (GC)-derived detectors, with custom-built and free standing detectors, or with detectors operated in metallic, ceramic, glass or polymeric microfluidic platforms. The chromatographic systems include supercritical fluid chromatographic systems and carbon dioxide based chromatographic systems.

Figure 2:
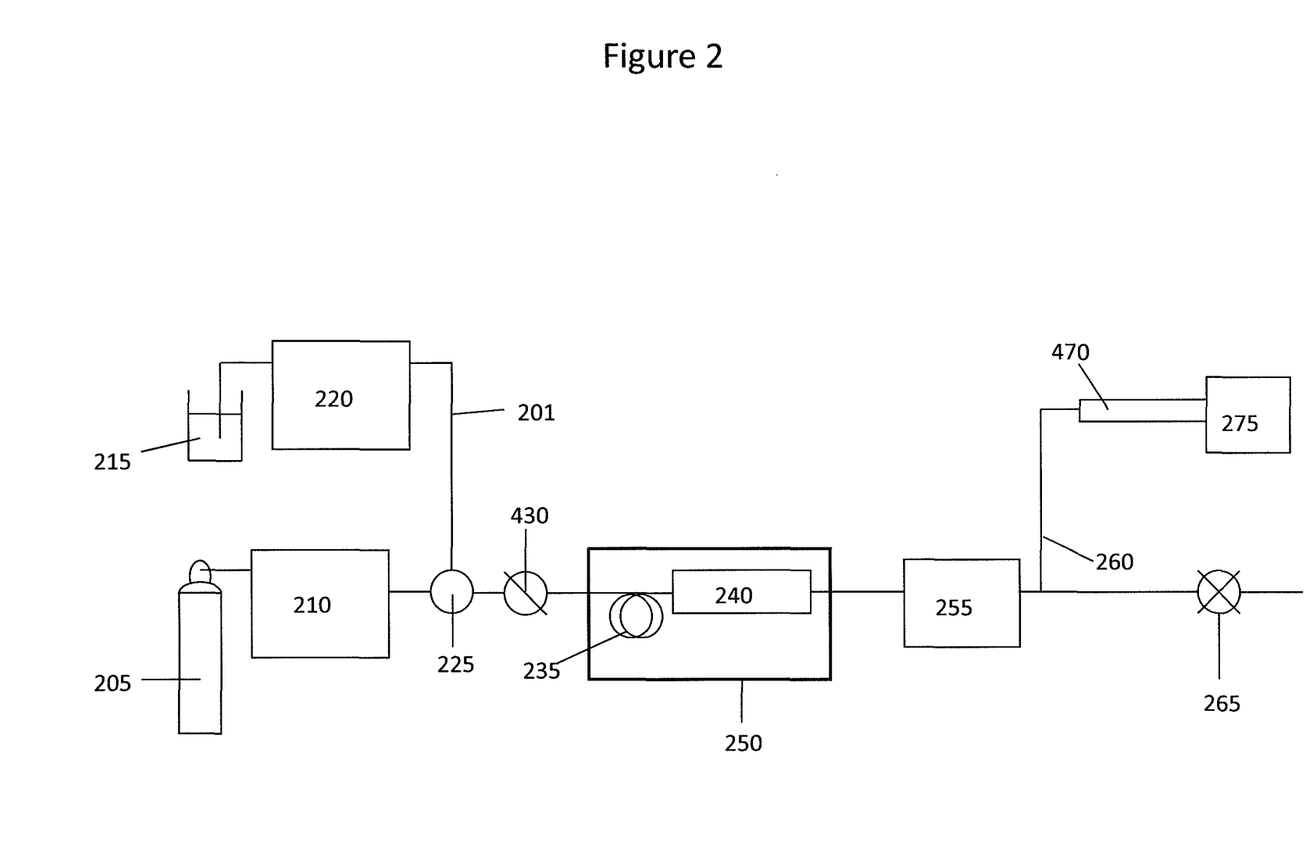
FIG. 2 is a schematic of a chromatographic apparatus employing an oxidizer to oxidize at least a portion of a polar modifier prior to detection in a flame-based detector.

FIG. 2 shows another embodiment of the present disclosure. FIG. 2 shows a schematic diagram of a chromatographic system employing the oxidizer of the present disclosure. The mobile phase is carbon dioxide. The system includes a number of components in fluid communication via the use of tubing (201). Carbon dioxide is supplied via a $CO_2$ tank (205) and is pumped through the system by a $CO_2$ pump (210). The polar modifier (e.g. methanol) is held in a modifier reservoir (215) and is pumped via a modifier pump (220). The modifier is mixed with the $CO_2$ mobile phase in a mixer (225). Samples (e.g. mixtures of organic compounds) can be injected through the sample injector (430). Samples are carried through the system under the action of a mobile phase (e.g. carbon dioxide and polar modifier). The sample is carried through a preheating portion (235) and a separation column (240), both of which can be kept at a constant temperature within a column oven (250). The mobile phase and sample then pass through an optional optical detector (255). The mobile phase can be spilt by a restrictor (260) that directs a portion of the mobile phase to exit through a back pressure regulator (265). Another portion of the mobile phase can be directed first to a catalytic element (470) to oxidize the polar modifier of the mobile phase before entering a flame-based detector (275) for detection of the analyte.

In addition to the above description, the following non-limiting examples are provided for illustrative purposes. The specification should not be understood as disclosing and encompassing all possible permutations and combinations of the described aspects, embodiments, and examples unless the context indicates otherwise. One of ordinary skill in the art will appreciate that the invention can be practiced by other than the summarized and described aspect, embodiments, and examples, which are presented for purposes of illustration, and that the invention is limited only by the following claims.

Example 1—FID

An analytical chromatographic system having an autosampler, a column oven, a chromatographic column and an automated back pressure regulator is provided. The mobile phase includes carbon dioxide and 20% methanol as a polar modifier and is supplied to the system via a fluid delivery module. The mobile phase is maintained at a pressure of 110 bar and the column is heated to a temperature of 40° C. The flow rate is 2.5 mL/min. The sample injection volume is 3 µL. At the outlet of the column, and upstream of the backpressure regulator, oxidizer packed with platinum mesh supported on particles of zirconia. The oxidizer is 10 cm long with an internal diameter of 1 cm. The mobile phase is flowed through the oxidizer via an inlet port and exits the oxidizer via an outlet port. The oxidizer is directly connected to, and in fluid communication with, a flame ionization detector at the outlet port and the analyte of interest is detected by the flame ionization detector and analyzed using software (e.g. Empower® 3 Chromatography Data Software; commercially available from Waters Technologies Corporation, Milford, Mass., USA).

Example 2—FPD

An analytical chromatographic system having an autosampler, a column oven, a chromatographic column and an automated back pressure regulator is provided. The mobile phase includes carbon dioxide and 20% methanol as a polar modifier and is supplied to the system via a fluid delivery module. The mobile phase is maintained at a pressure of 110 bar and the column is heated to a temperature of 40° C. The flow rate is 2.5 mL/min. The sample injection volume is 3 μL. At the outlet of the column, and upstream of the backpressure regulator, is a tee fitting directs a portion of the mobile phase flow to the BPR and a portion of the mobile phase flow to an oxidizer packed with platinum mesh supported on particles of zirconia. The oxidizer is 10 cm long with an internal diameter of 1 cm. The mobile phase is flowed through the oxidizer via an inlet port and exits the oxidizer via an outlet port. The oxidizer is directly connected to, and in fluid communication with, a flame photometric detector at the outlet port and the analyte of interest is detected by the flame photometric detector and analyzed using software (e.g. Empower® 3 Chromatography Data Software; commercially available from Waters Technologies Corporation, Milford, Mass., USA).

Example 3

A supercritical fluid chromatography system equipped with a chromatographic column (e.g., a 3.0×100 mm, 1.7 μm column) is used to separate a mixture of positional isomers. The eluent includes Mobile Phase A (carbon dioxide) and Mobile Phase B (methanol with 0.2% formic acid). A wash solvent comprising isopropyl alcohol is used. The eluent in the column is maintained at a pressure of 2175 psi and a temperature of 60° C. The flow rate is 1.2 mL/min.

A sample is prepared comprising all six positional isomers of dimethoxybenzoic acid (DMBA). The compounds are dissolved together in isopropyl alcohol, each at a concentration of 0.2 mg/mL. The sample is then injected into the system (injection volume: 1.0 μL). A chromatographic separation is performed within 4.5 minutes according to the following solvent gradient:

| Time (min) | Mobile Phase B % |
| --- | --- |
| 0 | 4 |
| 0.15 | 4 |
| 2.75 | 12 |
| 4 | 25 |
| 4.35 | 25 |
| 4.5 | 4 |

Figure 3:
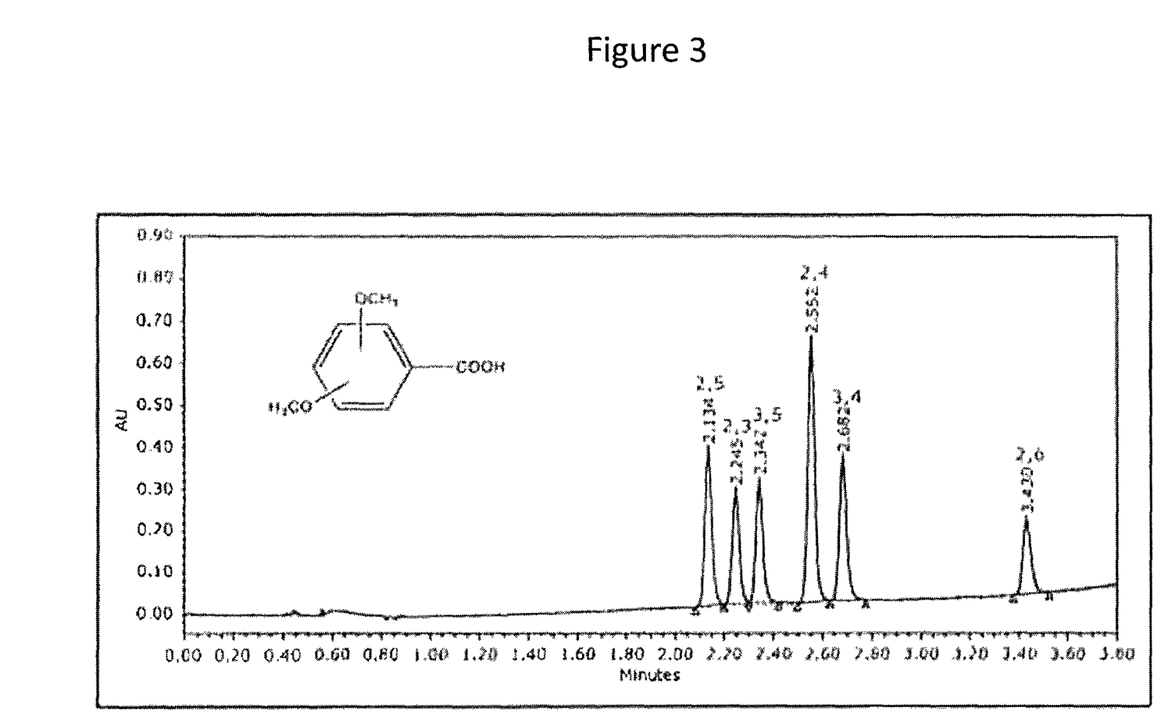
FIG. 3 is a chromatogram illustrating the use of oxidizer in a supercritical fluid chromatographic system.

The analytes were separated using the system described herein and detected with a photodiode array (PDA) detector at 240 nm using software (e.g. Empower® 3 Software; commercially available from Waters Technologies Corporation, Milford, Mass., USA). FIG. 3 shows the separation using the PDA detector. It is expected that the use of a flame ionization detector (FID) in the absence of the oxidizer of the present disclosure would fail to produce a clear, reliable signal and equivalent chromatogram due to the interference from methanol (mobile phase B) in the eluent reacting in the FID. It is expected, however, that the use of an oxidizer of the present disclosure would reduce the amount of methanol entering the detector to levels low enough to enable the use of a flame ionization detector to produce a chromatogram similar to that shown in FIG. 3.

What is claimed is:

1. A method of oxidizing a polar modifier in a chromatographic mobile phase containing at least one analyte of interest, comprising:
   (i) providing a chromatographic system having a separation column, an oxidizer in fluid communication with and downstream of the column, and a flame-based detector in fluid communication with and downstream of the oxidizer; and
   (ii) oxidizing at least a portion of the polar modifier consisting essentially of methanol in the oxidizer to carbon dioxide, wherein the oxidizer has a catalyst that (a) facilitates selective oxidation of at least a portion of the polar modifier to carbon dioxide which does not substantially produce a signal in the flame-based detector and (b) does not permit the complete oxidation of the at least one analyte of interest.

2. The method of claim 1, wherein the mobile phase comprises carbon dioxide.

3. The method of claim 1, wherein the flame-based detector is a flame ionization detector or a flame photometric detector.

4. The method of claim 1, wherein the catalyst comprises one or more constituents selected from the group consisting of: Ag, Au, Rh, Ni, Cd, Pt, Pd, Cu, $TiO_2$, ZnO, $ZrO_2$, and $Al_2O_3$; or combinations, alloys, or mixtures thereof.

5. The method for claim 1, wherein the oxidizer further comprises a reagent gas.

6. The method of claim 1, wherein the catalyst is deposited on the surface of a ceramic support.

7. The method of claim 1, wherein the oxidizer further comprises a heater in thermal communication with the oxidizer wherein the heater is capable of maintaining the catalyst at a temperature range.

8. The method of claim 1, wherein over 50 wt % of the polar modifier in the mobile phase entering the oxidizer is oxidized.

9. The method of claim 1, wherein the polar modifier in the mobile phase entering the oxidizer is substantially completely oxidized.

10. A chromatographic system comprising
   a mobile phase source;
   a polar modifier source;
   a sample source;
   a separation column in fluid communication with each of the mobile phase source, the polar modifier source, and the sample source and which receives therefrom a combined flow of mobile phase, polar modifier consisting essentially of methanol, and sample;
   an oxidizer comprising:
   (i) an inlet port that receives the combined flow from the separation column;
   (ii) a chamber in fluid communication with the inlet port, wherein the chamber has a catalyst configured to (a) facilitate selective oxidation of at least a portion of the polar modifier to carbon dioxide which does not substantially produce a signal in a flame-based detector and (b) does not permit the complete oxidation of at least one analyte of interest within the sample; and
   (iii) an outlet port in fluid communication with the chamber for exiting the mobile phase and carbon dioxide from the chamber; and
   the flame-based detector in fluid communication with the outlet port.

11. The chromatographic system of claim 10, wherein the mobile phase comprises carbon dioxide.

12. The chromatographic system of claim 10, wherein the flame-based detector is a flame ionization detector or a flame photometric detector.

13. The chromatographic system of claim 10, wherein the catalyst comprises one or more constituents selected from the group consisting of: Ag, Au, Rh, Ni, Cd, Pt, Pd, Cu, $TiO_2$, ZnO, $ZrO_2$, and $Al_2O_3$; or combinations, alloys, or mixtures thereof.

14. The chromatographic system of claim 10, further comprising a reagent gas in the chamber.

15. The chromatographic system of claim 10, wherein the catalyst is deposited on the surface of a ceramic support.

16. The chromatographic system of claim 10, further comprising a heater in thermal communication with the chamber wherein the heater is capable of maintaining the catalyst at a temperature range.

17. The chromatographic system of claim 10, wherein over 50 wt % of the polar modifier in the mobile phase entering the chamber is oxidized.

18. The chromatographic system of claim 10, wherein the polar modifier in the mobile phase entering the chamber is substantially completely oxidized.

* * * * *